United States Patent
Khandaker et al.

(10) Patent No.: US 9,809,906 B2
(45) Date of Patent: Nov. 7, 2017

(54) METHOD AND APPARATUS TO COAT A METAL IMPLANT WITH ELECTROSPUN NANOFIBER MATRIX

(71) Applicant: UNIVERSITY OF CENTRAL OKLAHOMA, Edmond, OK (US)

(72) Inventors: Morshed Khandaker, Edmond, OK (US); Shahram Riahinezhad, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 0 days.

(21) Appl. No.: 15/467,652

(22) Filed: Mar. 23, 2017

(65) Prior Publication Data
US 2017/0275783 A1    Sep. 28, 2017

Related U.S. Application Data

(63) Continuation-in-part of application No. 14/734,147, filed on Jun. 9, 2015.
(Continued)

(51) Int. Cl.
*A61F 2/28* (2006.01)
*D01D 11/06* (2006.01)
(Continued)

(52) U.S. Cl.
CPC ............ *D01D 11/06* (2013.01); *A61F 2/28* (2013.01); *A61F 2002/2817* (2013.01);
(Continued)

(58) Field of Classification Search
CPC ............ A61F 2/28; A61F 2002/2817; A61F 2002/30677; A61F 2002/0068;
(Continued)

(56) References Cited

U.S. PATENT DOCUMENTS

| 692,631 A | 2/1902 | Cooley |
| 1,975,504 A | 10/1934 | Formhals |

(Continued)

FOREIGN PATENT DOCUMENTS

| CN | 1687493 A | 10/2005 |
| CN | 1766181 A | 5/2006 |

(Continued)

OTHER PUBLICATIONS

Yarin et al., "Branching in electrospinning of nanofibers", Journal of Applied Physics 98, pp. 064501, 2005, pp. 1-12.
(Continued)

*Primary Examiner* — Alvin Stewart
(74) *Attorney, Agent, or Firm* — Berenato & White, LLC

(57) ABSTRACT

The present invention implements a set of grooves/ridges created on Ti at the circumferential direction to increase surface area of implant in contact with bone. These grooves/ridges protect nanofiber matrix (NFM) made with Polycaprolactone (PCL) electrospun nanofiber (ENF) and collagen at the groove from physiological loading. Controlled fabrication of a ridge made with titanium nitride (TiN) around the circumference of Ti is provided using a plasma nitride deposition technique. PCL ENF may be deposited along the sub-micrometer grooves using the electrospin setup disclosed. The method provides for fabrication of microgroove on Ti using machining or TiN deposition and filling the microgrooves with the NFM. This method has proven through experimentation to be successful in increasing in vivo mechanical stability and promoting osseointegration on Ti implants. The immobilization of MgO NP and FN with the PCL-CG NFM on microgrooved Ti as provided in the invention optimizes biological performances of Ti.

15 Claims, 20 Drawing Sheets

Related U.S. Application Data

(60) Provisional application No. 62/312,041, filed on Mar. 23, 2016, provisional application No. 62/038,506, filed on Aug. 18, 2014.

(51) Int. Cl.
*A61F 2/30* (2006.01)
*D01D 5/00* (2006.01)

(52) U.S. Cl.
CPC ............... *A61F 2002/30677* (2013.01); *A61F 2310/00023* (2013.01); *D01D 5/0007* (2013.01); *D10B 2331/041* (2013.01); *D10B 2509/00* (2013.01)

(58) Field of Classification Search
CPC .......... A61F 2002/30042; A61F 2/0063; A61F 2002/3006; A61F 2002/30062; A61F 2002/30065; A61F 2002/30067; A61B 17/12168; A61B 17/8085
USPC ........................................... 623/23.29–23.31
See application file for complete search history.

(56) References Cited

U.S. PATENT DOCUMENTS

| | | | |
|---|---|---|---|
| 2,109,333 A | 2/1938 | Formhals | |
| 2,123,992 A | 7/1938 | Formhals | |
| 2,187,306 A | 1/1940 | Formhals | |
| 2,349,950 A | 5/1944 | Formhals | |
| 4,536,894 A * | 8/1985 | Galante | A61F 2/30907 623/23.3 |
| 4,636,219 A * | 1/1987 | Pratt | A61F 2/30907 228/193 |
| 4,655,769 A * | 4/1987 | Zachariades | A61L 27/16 138/103 |
| 5,013,324 A * | 5/1991 | Zolman | A61F 2/30907 623/23.3 |
| 5,370,698 A * | 12/1994 | Heimke | A61F 2/30767 623/22.15 |
| 5,507,833 A * | 4/1996 | Bohn | A61F 2/32 623/23.3 |
| 5,672,284 A * | 9/1997 | Devanathan | A61F 2/30907 219/121.64 |
| 6,106,913 A | 8/2000 | Scardino et al. | |
| 6,312,473 B1 * | 11/2001 | Oshida | A61F 2/30907 623/22.33 |
| 6,355,699 B1 | 3/2002 | Vyakarnam et al. | |
| 6,743,273 B2 | 6/2004 | Chung et al. | |
| 6,753,454 B1 | 6/2004 | Smith et al. | |
| 6,821,479 B1 | 11/2004 | Smith et al. | |
| 7,575,707 B2 | 8/2009 | Xia | |
| 7,828,539 B1 | 11/2010 | Beachley et al. | |
| 7,879,093 B2 * | 2/2011 | Wei | 424/422 |
| 8,157,554 B2 | 4/2012 | Petras et al. | |
| 8,475,531 B1 * | 7/2013 | Maxson | A61F 2/30756 623/14.12 |
| 8,691,542 B2 * | 4/2014 | Guilak | A61L 27/54 424/422 |
| 9,095,524 B2 * | 8/2015 | Warnke | A61K 9/7007 |
| 9,180,223 B2 * | 11/2015 | Yu | A61L 27/3852 |
| 9,359,694 B2 | 6/2016 | Khandaker et al. | |
| 9,649,409 B2 * | 5/2017 | Guilak | A61L 27/54 |
| 2005/0104606 A1 | 5/2005 | Donsky | |
| 2005/0137675 A1 | 6/2005 | Dubson et al. | |
| 2005/0142163 A1 * | 6/2005 | Hunter | A61B 17/11 424/423 |
| 2005/0224998 A1 | 10/2005 | Andrady et al. | |
| 2005/0276841 A1 * | 12/2005 | Davis | A61K 9/0051 424/443 |
| 2006/0226580 A1 | 10/2006 | Xia et al. | |
| 2007/0269481 A1 | 11/2007 | Li et al. | |
| 2007/0275458 A1 | 11/2007 | Gouma | |
| 2008/0170982 A1 | 7/2008 | Zhang et al. | |
| 2008/0290554 A1 | 11/2008 | Wu et al. | |
| 2009/0118813 A1 | 5/2009 | Scheuermann et al. | |
| 2009/0196901 A1 * | 8/2009 | Guilak | A61L 27/54 424/423 |
| 2009/0226600 A1 | 9/2009 | Dang et al. | |
| 2009/0294733 A1 | 12/2009 | Branham et al. | |
| 2009/0324680 A1 * | 12/2009 | Reneker | A61L 31/042 424/423 |
| 2009/0324950 A1 | 12/2009 | Kim | |
| 2010/0009267 A1 * | 1/2010 | Chase | B01D 39/2082 429/320 |
| 2010/0028387 A1 | 2/2010 | Balasundaram et al. | |
| 2010/0113857 A1 | 5/2010 | Ramakrishna et al. | |
| 2010/0119578 A1 | 5/2010 | To et al. | |
| 2010/0168771 A1 * | 7/2010 | Guldberg | A61L 27/3804 606/151 |
| 2010/0197027 A1 | 8/2010 | Zhang et al. | |
| 2010/0310623 A1 * | 12/2010 | Laurencin | A61F 2/28 424/423 |
| 2010/0327494 A1 | 12/2010 | Jabbari | |
| 2010/0331980 A1 * | 12/2010 | Lee | A61L 27/26 623/14.13 |
| 2011/0066242 A1 * | 3/2011 | Lu | A61K 38/18 623/13.14 |
| 2013/0030452 A1 * | 1/2013 | Itskovitz-Eldor | A61L 27/34 606/151 |
| 2013/0110138 A1 * | 5/2013 | Hurtado | A61F 2/00 606/152 |
| 2013/0273801 A1 | 10/2013 | Young | |
| 2014/0205971 A1 | 7/2014 | Wang | |
| 2014/0271786 A1 * | 9/2014 | Bagga | A61L 27/56 424/443 |
| 2014/0271795 A1 * | 9/2014 | Phaneuf | A61K 31/496 424/443 |
| 2015/0273110 A1 * | 10/2015 | McClellan | A61L 27/34 427/2.24 |
| 2015/0290354 A1 * | 10/2015 | Loboa | A61L 15/22 424/447 |
| 2016/0047063 A1 * | 2/2016 | Khandaker | D01D 5/0076 425/174.8 E |
| 2016/0047064 A1 | 2/2016 | Khandaker et al. | |
| 2016/0250393 A1 * | 9/2016 | Jeong | A61L 27/54 424/425 |
| 2016/0374820 A1 * | 12/2016 | Khandaker | A61F 2/441 623/17.12 |
| 2017/0072089 A1 * | 3/2017 | Nseir Manassa | B32B 7/02 |
| 2017/0130194 A1 * | 5/2017 | Lee | C12N 5/0068 |
| 2017/0143874 A1 * | 5/2017 | Vickers | A61L 31/041 |
| 2017/0167064 A1 * | 6/2017 | Taylor | D04H 1/728 |

FOREIGN PATENT DOCUMENTS

| | | |
|---|---|---|
| CN | 1776033 A | 5/2006 |
| WO | WO2004074559 A1 | 9/2004 |
| WO | WO2005073442 A1 | 8/2005 |
| WO | WO2005123995 A1 | 12/2005 |
| WO | WO2006052039 A1 | 5/2006 |
| WO | WO2006135147 A1 | 12/2006 |

OTHER PUBLICATIONS

Ali et al., "Electrospinning of Continuous Nanofiber Bundles and Twisted Nanofiber Yarns", Nanofibers—Production, Properties and Functional Applications, 2011, pp. 153-174.

Bashar Haseeb, "Controlled deposition and alignment of electrospun PMMA-g-PDMS nanofibers by novel electrospinning setups", Master of Science Thesis, KTH Chemical Science and Engineering, Stockholm, Sweden 2011, 164 pages.

KdScientific, "Inflowmation Chronicles Highlights of Interesting Scientific Applications", Inflowmation Chronicles, Issue 1001, Spring 2009, 2 pages.

Li et al., "Electrospinning of Nanofibers: Reinventing the Wheel**", Advanced Materials, 2004, vol. 16, No. 14, pp. 1151-1170.

Monika Rajput, "Optimization of Electrospinning Parameters to Fabricate Aligned Nanofibers for Neural Tissue Engineering", A

(56) References Cited

OTHER PUBLICATIONS

Thesis Submitted in Partial Fulfillment of the Requirement for the Degree of Master Of Technology in Biotechnology & Medical Engineering, Department of Biotechnology and Medical Engineering, National Institute Of Technology, Rourkela, Orissa, India, 2012, 74 pages.
Neves et al., "Patterning of polymer nanofi ber meshes by electrospinning for biomedical applications", International Journal of Nanomedicine, 2007, 2(3), pp. 433-448.
Peterson, "Hybrid Nanomanufacturing Process for High-Rate Polymer Nanofiber Production", University of Nebraska—Lincoln, DigitalCommons@University of Nebraska—Lincoln, Engineering Mechanics Dissertations & Theses, 2010, 159 pages.
Tan et al., "Tensile testing of a single ultrafine polymeric fiber", Biomaterials 26, 2005, pp. 1453-1456.
Theron et al., "Electrostatic field-assisted alignment of electrospun nanofibres", Nanotechnology, 12, 2001, pp. 384-390.
Hickey et al. Adding MgO nanoparticles to hydroxyapalite-PPLA Nanocomposites for Improved Bone Tissue Engineering Applications, Acta Biomaterialia, 2015, 11 pages.
Xie et al. Silver Nanoparticles and Growth Factors Incorporated Hydroxyapatite Coatings on Metallic Implant Surfaces for Enhancement of Osteoinductivity and Antibacterial Properties, ACS Appl. Mater. Interfaces, 2014, 2 pages.
Liu et al Surface modification of titanium, titaniaum alloys, and related materials for biomedical applications., Materials Science and Engineering R 47 (2004), 73 pages.
Corresponding ISR and Written Opinion dated Jun. 19, 2017.

\* cited by examiner

METHOD AND APPARATUS TO COAT A METAL IMPLANT WITH ELECTROSPUN NANOFIBER MATRIX

CROSS REFERENCES TO RELATED APPLICATIONS

This application claims the benefit of U.S. Provisional Patent Application No. 62/312,041 filed on Mar. 23, 2016 in the name of Morshed Khandaker and Shahram Riahinezhad, which is expressly incorporated herein by reference in its entirety. This application is a continuation-in-part of U.S. patent application Ser. No. 14/734,147 filed Jun. 9, 2015 by the University of Central Oklahoma (Applicant), entitled "Method and apparatus for controlled alignment and deposition of branched electrospun fiber". This application also claims the benefit of U.S. Provisional Patent Application No. 62/038,506 filed on Aug. 18, 2014 in the name of Morshed Khandaker and William Paul Snow.

STATEMENT AS TO RIGHTS TO INVENTIONS MADE UNDER FEDERALLY SPONSORED RESEARCH OR DEVELOPMENT

This invention was made with government support under Grant Number 8P20GM103447 awarded by the National Institutes of Health. The government has certain rights in the invention.

FIELD OF THE INVENTION

The present invention generally relates to the field of polymer fiber production in relation to the field of prosthetics. More specifically, the invention relates to the attachment of fibers exhibiting micron to nano size diameters on different shapes of metallic implants from the nanofiber matrix produced in an electrospin process.

BACKGROUND OF THE INVENTION

Polycaprolecton (PCL) Electrospun Nanofibers (ENF) have numerous biomedical applications. Co-pending application Ser. No. 14/734,147 and U.S. Pat. No. 9,359,694 by the present Applicant disclose a method and apparatus for controlled deposition of branched ENF on biomedical implants and material. ENF have been found to be excellent carriers of drugs for improving the bone growth around a bio-medical implant. If applied as a coating around the implant, improved bone growth may reduce the implant loosening problem widely experienced with presently available implants. However, the use of PCL ENF matrix as a coating material for an implant has heretofore been severely limited because ENF fiber has poor adhesion with an implant surface, preventing use at physiological load bearing conditions.

An ideal implant for total joint arthroplasty or dental surgeries has not yet been developed. When an implant is inadequate for osseointegration, micro-motions occur at the implant surface leading to activation of osteoclasts' resorption of bone around the implant, contributing to further implant loosening and eventual implant failure. Delayed bone healing has been reported in approximately 600,000 fractures per year in the United States. Along with the physical pain and suffering, implant loosening due to poor osseointegration and healing leads to economic burdens with the direct medical costs exceeding $3 billion alone annually. A method is needed to attach the ENF fibers to an implant surface for both regular and irregular shape implants. This method will also need to enable drug delivery and promote bone growth.

SUMMARY OF THE INVENTION

The process of the present invention provides methods to achieve adhesion of functional nanofiber coatings on a biomedical implant surface to increase the osteoinductive properties, and thereby to improve osseointegration of implant. The effects of fibers on the mechanical stability and osseointegration of an implant with and without fibers have not yet been known. In one aspect, a specific objective of the present invention is to provide methods to attach ENF fibers to an implant surface. The methods provided by the present invention can be used for both regular and irregular shape implants.

The process of the present invention provides a method for coating a metal (e.g., titanium) implant with a functional coating made with PCL ENF and includes a set of steps by which PCL ENF can be bonded with the metal implant. The method of the present invention can be implemented with the controlled electrospinning methods and apparatus disclosed herein, as well as in co-pending application Ser. No. 14/734,147 by the present Applicant, which methods are incorporated herein by reference in the entirety. The method of the present invention can also be implemented with other methods and processes for producing and applying micro to nano scale fibers to substrates.

The present invention implements a set of grooves/ridges that are created on titanium (Ti) at the circumferential direction to increase the surface area of implant in contact with bone. These grooves/ridges protect the nanofiber matrix (NFM) made with Polycaprolactone (PCL) electrospun nanofiber (ENF) and collagen (CG) at the groove from physiological loading.

The present invention provides controlled fabrication of a microgrooves made with machine sawing, laser indentation, and titanium nitride (TiN) ion deposition around the circumference of Ti using a plasma nitride deposition technique. PCL ENF may be deposited along the sub-micrometer grooves with the help of plasma oxidation and collagen on Ti implant using a set of steps disclosed in this application. This method has proven through experimentation to be successful in increasing the in vivo mechanical stability and promoting osseointegration on Ti implants. The automatic production of micron to nano size grooves by laser indentation and TiN deposition as provided by the invention optimizes the groove topography on Ti. An extensive search of the related art revealed no reported research directed to the coating of Ti implant by NFM in relation to the influence of machine sawing, laser and TiN topography on the mechanical and biological performances of Ti.

The method for PCL ENF-CG coating on titanium as provided by the present invention provides at least the following unique features:

1. The combined tailoring of interdigitation sites on Ti implant through microgrooving incorporated surface roughness to the implant and deposition of electrospun nanofiber matrix (NFM) on the grooving sites.

2. The use of a machine sawing technique, is uniquely used to create controlled microgrooves on the circumference on Ti.

3. The use of nitrogen plasma, applied in semiconductor industry for nanoscale surface modification, is uniquely used to create TiN ridges on flat and circumference sides of a Ti rod.

4. The effects of the fiber diameter in PCL-CG NFM at the groove of Ti on the Ti-bone interaction may be enhanced to provide better bonding.

5. The effects of the attachment of osteoconductive nanoparticles (MgO) with PCL-CG nanofiber matrix at the groove of Ti on the Ti-bone interaction may be enhanced to provide better bonding.

6. At the groove, other biological glue such as PMMA cement, fibronectin, 2-octyl cyanoacrylate may be used to attach the PCL ENF.

In another aspect, microgrooves are fabricated on an implant by controlled formation of titanium nitride (TiN) ridges and the microgrooves are coated by CG-PCL NFM to produce higher biomechanical advantages compared to non-coated Ti implants due to increased biological compatibility of NFM coated Ti.

In another aspect, fibronectin (FN) and magnesium oxide nanoparticles (MgO NPs) immobilized PCL NFM coating are coupled with tresyl chloride-activated Ti implant to produce higher biomedical advantages compared to CG-PCL NFM due to the increased osteoinductive nature of the coatings.

In another aspect, CG-PCL NFM coating is used to act as resource for bone growth molecules (TGF-β, rhBMP) and antimicrobial agents (MgO, ZnO, Ag) to the adjoining bone tissue to have better osseointegration with the implant surface.

DETAILED DESCRIPTION OF PREFERRED EMBODIMENTS OF THE INVENTION

Figure 1:
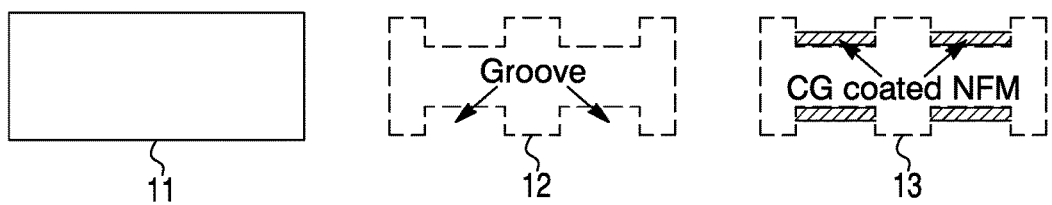
FIG. 1 is a non-limiting diagram showing the schematic images of longitudinal cross-section of a Ti rod without grooves, with circumferential grooves, and with circumferential grooves and nanofiber matrix (NFM) applied.

Referring now to FIG. 1, a non-limiting diagram shows schematic images of a longitudinal cross-section of a Ti rod without grooves 11, with circumferential grooves 12, and with circumferential grooves and nanofiber matrix (NFM) applied 13. The process of the present invention provides a method for controlled fabrication of microgrooves 12 around the circumference of a Ti implant 11. The present invention provides techniques to attach ENF fibers to an implant surface as shown positioned within the groves 13.

Figure 2:
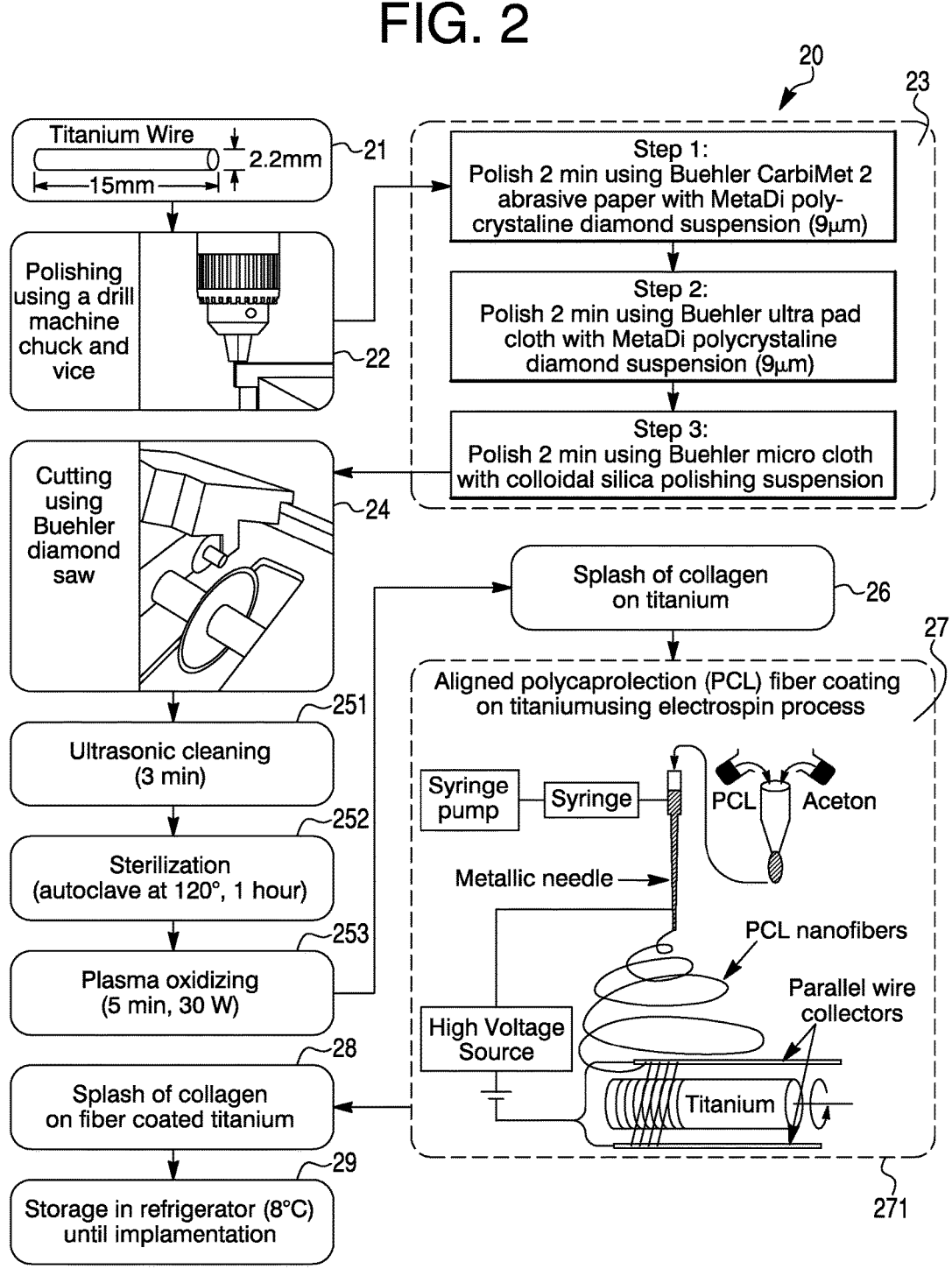
FIG. 2 is a non-limiting diagram showing a schematic representation of the process of the present invention for creating of microgrooves on Ti using machine sawing and depositing PCL-CG ENF on a Ti implant.
Figure 8:
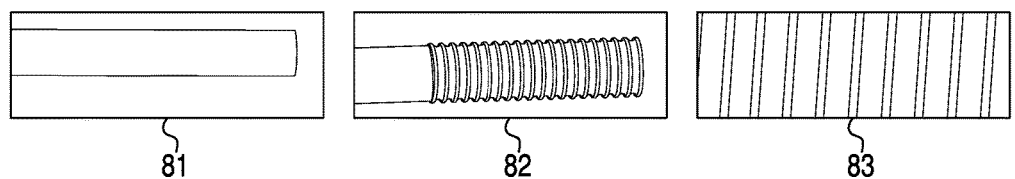
FIG. 8 is a non-limiting diagram showing a sample Ti rod fabricated without grooves 81, with grooves 82, and with grooves and nanofiber matrix (NFM) 83 applied using the methods of the present invention.

Referring now to FIG. 2, a non-limiting diagram shows the process of the present invention providing a method 20 for coating a metal implant with electrospun nanofiber, and includes a set of steps (shown in block diagram) by which PCL ENF can be bonded with the metal implant [See FIG. 8, 83]. Briefly, a Ti implant 21 (e.g., 2.2 mm×15 mm wire) may be polished using a drill machine chuck and gripper 22. Other functionally equivalent rotating devices may be used. A Ti implant may be secured at a drill chuck or by clamps on another type rotating device, and a polish paper (10 mm×50 mm) wrapped around the Ti implant with pressure using the gripper of the drill machine 22. Polishing can occur when the drill machine 22 or other rotating device is in operation. Ti wires samples have been circumferentially polished up to 8 mm from one end using this method. Similar results can be achieved for other cylindrical implants. The three steps polishing technique 23, as recommended by Buehler, Ltd., Evanston, Ill., can be used to polish the Ti implant. Other polishing techniques are possible. A diamond saw blade (Buehler Isomet wafer blade, 0.15 mm thickness, 15HC available from Buehler, Ltd., Evanston, Ill.) may be used to machine the microgroove on the circumferential surface of the implant (e.g., wire) 24. Ti implant (e.g., wire) can be fastened to the shaft of an electric motor or other type rotating machine 24. The motor can be secured in the saw machine 24 at the implant grip holder. Each microgroove can be created by running the motor and saw machine simultaneously in opposite directions for 8 seconds. In one preferred embodiment of the present invention, eighteen bands of circumferential parallel grooves are created starting at a 0.5 mm distance from one end of the Ti wire. The microgrooves are fabricated 0.05 mm apart from each other. The implant (e.g., wire) is then cleaned 251 in an ultrasonic cleaner followed by 70% ethanol wash 252 and autoclaved at 121° C. The Ti implant (e.g., wire) having grooves is exposed 253 to plasma $O_2$ for 5 minutes in a Zepto low pressure reactive ion etching system (Frequency: 40 kHz, power 30 watt) to increase the attachment of collagen to the Ti surface. The Ti implant (e.g., wire) is soaked 26 with a collagen solution and PCL electrospun nanofiber is deposited 27 on the Ti surface. Aligned PCL nanofibers are deposited on the grooved Ti implant using an electrospin setup 27. In one preferred embodiment, aligned PCL fibers can be collected between two parallel collectors 271 (e.g., wires or opposing plates). In another preferred embodiment, the method of the present invention can be implemented with the controlled electrospinning methods and apparatus disclosed in co-pending application Ser. No. 14/734,147. Collagen solution can be prepared by mixing 2.3 microliters of type I collagen with 0.23 microliters of acetic acid (0.02 M) and 195 microliters of deionized water in a vortex mixer. The Ti implant (e.g., wire) may be soaked 26 with the collagen solution. Aligned PCL ENF can be deposited on the Ti surface by rotating the Ti implant at least 6 times and dried in UV chamber. Rotation of the Ti implant can be accomplished either manually or using the methods disclosed in co-pending application Ser. No. 14/734,147. Finally, CG solution coating on Ti implant can be applied again 28 and dried to prepare the groove-NFM Ti surface. The groove-NFM implant can be kept at 4 degrees C. until implantation in the recipient. The topography of fibers can be examined on a carbon tape using Hitachi™ 3000 scanning electron microscope. The carbon tape can be wrapped around a Ti rod and the fibers collected on the tape by manually rotating the rod in a manner similar to the way fibers are collected on Ti for implants.

Figure 3:
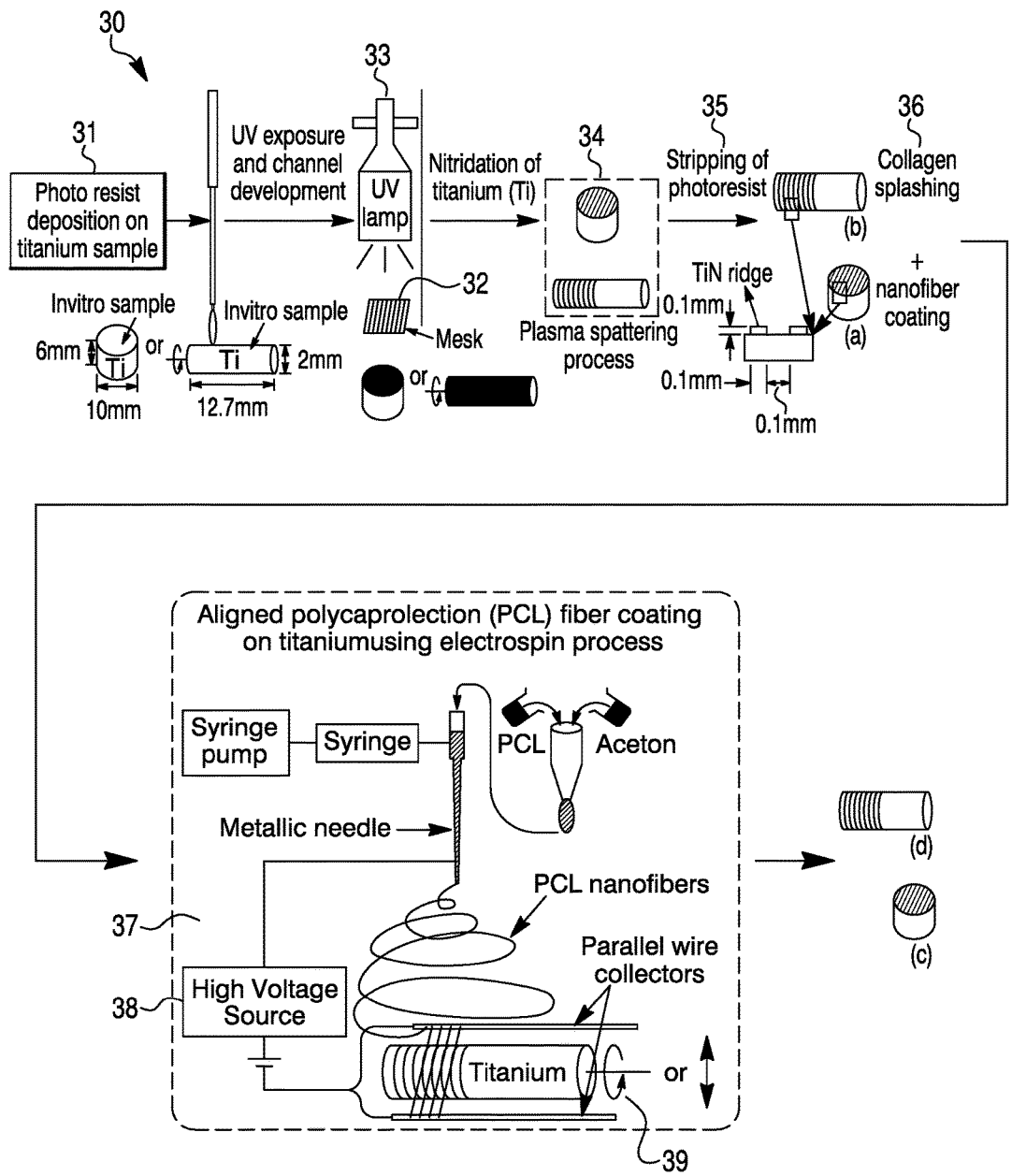
FIG. 3 is a non-limiting diagram showing a schematic representation of the method of the present invention providing controlled fabrication of ridge made with titanium nitride (TiN) around the circumference of a Ti substrate using a plasma nitride deposition technique.

Referring now to FIG. 3, a non-limiting diagram shows the process of the present invention providing a method 30 for creating TiN ridges on a Ti implant and PCL-CG coating on Ti implants having the TiN ridges. The FIG. 3 shows the formation of TiN ridges along the flat end surface of a Ti implant (e.g., 10 mm diameter×6 mm height) and the circumference surface of a Ti implant (e.g., 2.2 mm diameter×12 mm height). In a preferred embodiment, a thin film of Su8 photoresist 31 (available from MicroChem Corp., Westborough, Mass.) is used to cover the Ti surface excluding ridge sites. A mask 32 with channels is placed on the Ti implant and exposed for UV etching 33 to create 3D textures at the sites. Research-grade nitrogen gas (available from AirGas, Inc.) is spattered 34 on the Ti surface to create TiN coating. The TiN ridges are visible upon removal 35 of Su8 by a photoresist removing chemical (e.g., RemoverPG also available from MicroChem Corp). The grooves formed by TiN ridges are coated by NFM made with the application of thin layer collagen 36 and multilayers of PCL ENF 37. FIG. 3 includes the process of coating the implant with multilayers of ENF 37. In a preferred embodiment, PCL solution is prepared by ultrasonic mixing of 7.69 wt % of PCL pellets with acetone. The sonication process is carried out at approximately 80° C. for an about an hour. The PCL solution is poured into a glass syringe in an infusion pump for fiber production. PCL fibers are ejected from the glass syringe via charged needle. The needle is charged by a high voltage power source 38. The fibers are deposited between two parallel collectors (e.g., wires or plates) forming an aligned layer 39. In one embodiment, to collect multiple layers of fiber on a larger diameter (e.g. 10 mm) Ti implant, the Ti implant is brought into contact with the aligned fiber layer positioned between the collectors, then lowered and rotated 90° and the process repeated to collect another layer. To collect multiple layers of fiber on smaller diameter (e.g., 2 mm) Ti implants, Ti implants may be rotated with constant speed using a motorized stage. Rotating larger diameter Ti implants a constant speed provides an alternative method for capturing fiber layers on larger implants.

Figure 4:
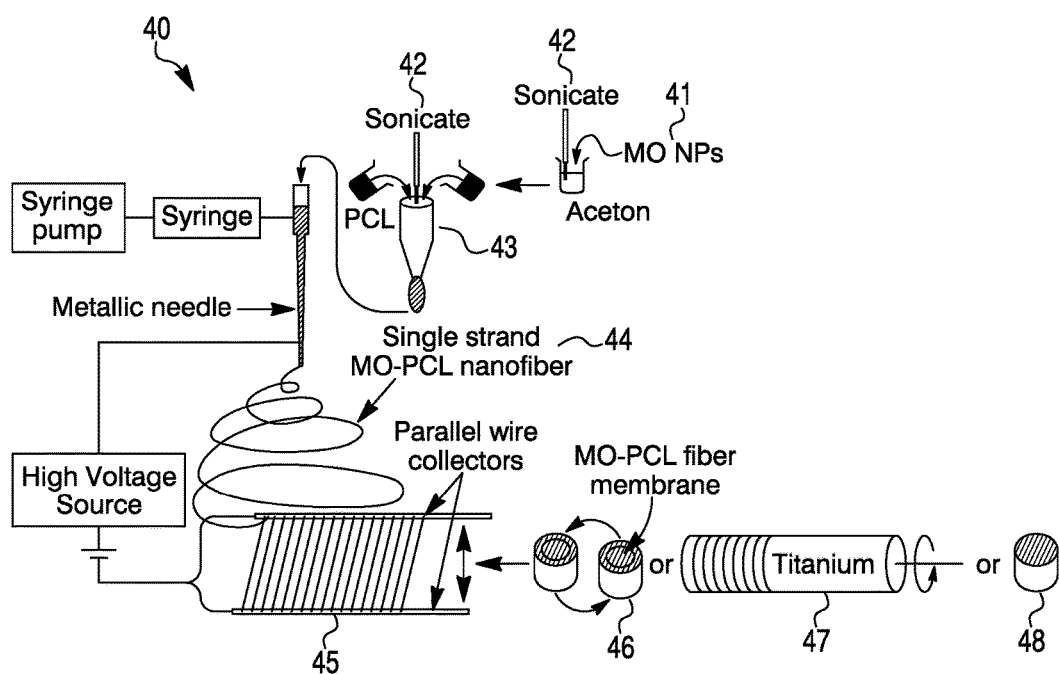
FIG. 4 is a non-limiting diagram showing the schematic representation of process for creating of microgrooves on Ti using machine sawing and depositing MgO nanoparticles immobilized PCL-CG ENF on the Ti.

Referring now to FIG. 4, a non-limiting diagram shows the process of the present invention providing a method 40 for tethering of metal oxide nanoparticles (MO NPs) with a single PCL nanofiber using the electrospin setup depicted in FIG. 3, 37. In a preferred embodiment, PCL solutions with different types of MO NPs are dissolved in acetone 41. Briefly, a 5 wt. % of each kind of NPs may be accurately weighed and sonicated 42 for 30 minutes to properly disperse in acetone. Then, PCL beads are added to the above solution so that the final solution contains 15 wt. % PCL, and the mixture sonicated 42 for another 30 minutes to ensure the dissolution of the PCL pellets and proper mixing with MO NPs. About 10 ml of the prepared solutions with MO-PCL solution may be taken in glass syringes 43 and electrospun 44 individually on two parallel collectors 45 (e.g., wire or plate) to produce aligned MO-PCL NFM. To collect multiple layers of fiber, an acrylic hollow cylindrical substrate 46 may be used to touch the aligned fiber stream, then lowered and rotated 90° and the process repeated to collect another layer on the substrate 46. Multi layers of aligned ENF can be coated on a Ti surface circumferentially by rotating the Ti implant with constant speed 47. Instead of using an acrylic substrate 46, Ti can be used to directly collect fiber on a Ti substrate 48 using the same method used for the acrylic substrate 46.

Figure 5:
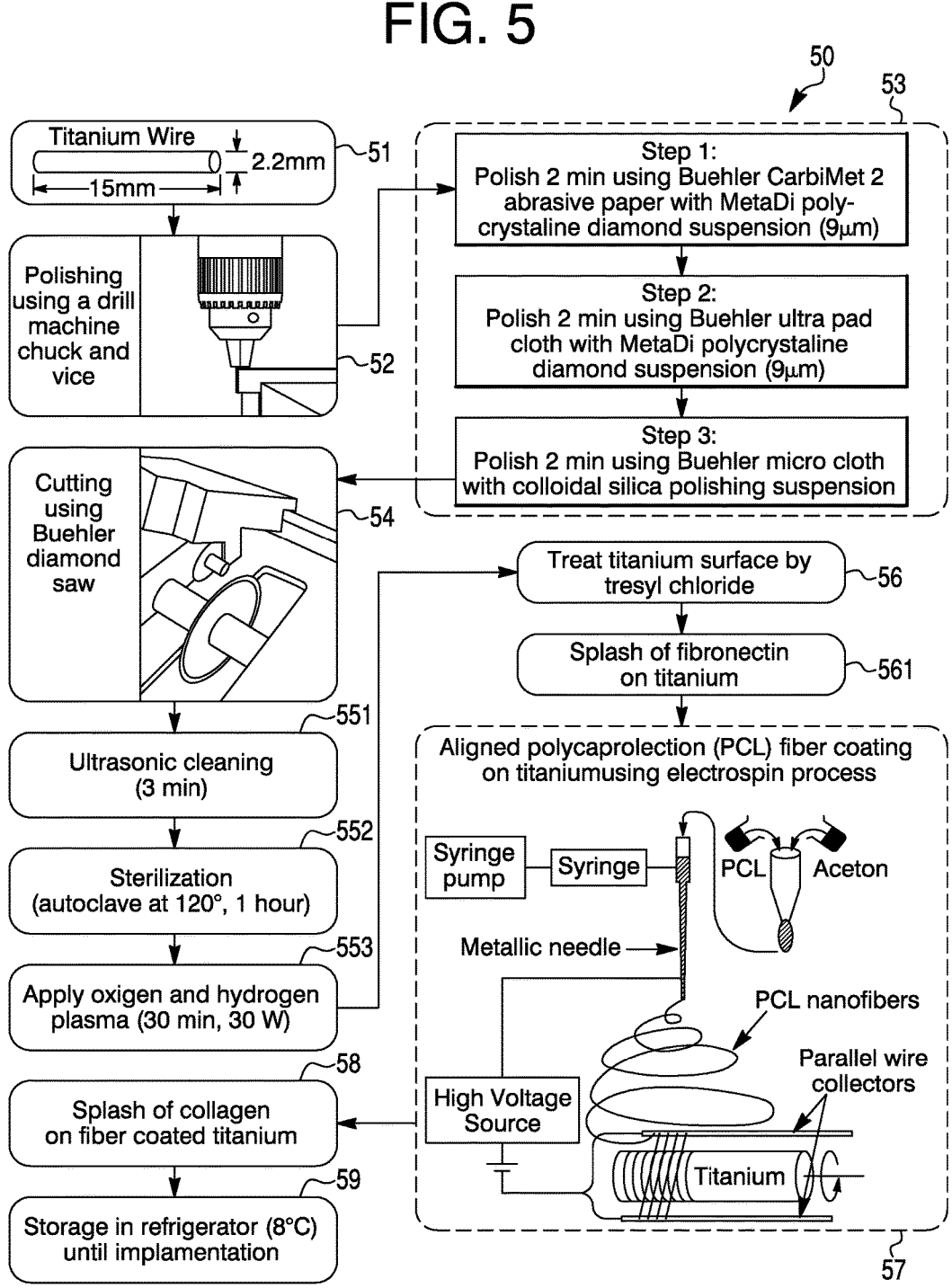
FIG. 5 is a non-limiting diagram showing the schematic representation of process for creating of microgrooves on Ti using machine sawing and depositing fibronectin immobilized Ti and PCL-CG ENF.

Referring now to FIG. 5, a non-limiting diagram shows the process of the present invention providing a method 50 for tethering of cellular fibronectin with titanium (Ti). A Ti implant 51 (e.g., 2.2 mm×15 mm wire) may be polished using a drill machine chuck and gripper 52. Other functionally equivalent rotating devices may be used. A Ti implant may be secured at a drill chuck or by clamps on another type rotating device, and a polish paper (10 mm×50 mm) wrapped around the Ti implant with pressure using the gripper of the drill machine 52. Polishing can occur when the drill machine 52 or other rotating device is in operation. Ti wires samples have been circumferentially polished up to 8 mm from one end using this method. Similar results can be achieved for other cylindrical implants. The three steps polishing technique 53, as recommended by Buehler, Ltd., Evanston, Ill., can be used to polish the Ti implant. Other polishing techniques are possible. A diamond saw blade (Buehler Isomet wafer blade, 0.15 mm thickness, 15HC available from Buehler, Ltd., Evanston, Ill.) may be used to machine the microgroove on the circumferential surface of the implant (e.g., wire) 54. Ti implant (e.g., wire) can be fastened to the shaft of an electric motor or other type rotating machine 54. The motor can be secured in the saw machine 54 at the implant grip holder. Each microgroove can be created by running the motor and saw machine simultaneously in opposite directions for 8 seconds. In one preferred embodiment of the present invention, eighteen bands of circumferential parallel grooves are created starting at a 0.5 mm distance from one end of the Ti wire. The microgrooves are fabricated 0.05 mm apart from each other. The implant (e.g., wire) is then cleaned 551 in an ultrasonic cleaner followed by 70% ethanol wash 552 and autoclaved at 121° C.

The titanium implant surface —OH activity is enhanced by combined application of oxygen and hydrogen in a plasma etcher. The Ti surface is activated 56 by tresyl chloride (2,2,2-trifluoroethanesulfonyl chloride, CF3CH2SO2Cl). Ti is completely covered with Tresyl chloride (TC) and then stored at 37° C. for 2 days. The Ti activated Ti implant is washed with water, water-acetone (50:50), and acetone and dried to produce tresyl chloride (TC) activated Ti surfaces. Human cellular fibronectin is dissolved in phosphate-buffered saline (PBS) solution with pH=7.4 at a concentration of 0.1 mg/mL. The TC activated Ti is immersed 561 into the fibronectin/PBS solution for 24 h at 37° C., then rinsed with double-distilled water. Finally, the Ti surfaces are dried with a gentle stream of dry air to produce FN immobilized Ti. PCL ENF is deposited 57 on the Ti surface described previously. PCL ENF is secured on Ti surface by splashing 58 second layer of FN and air drying the FN in a hood and storing the implant in a refrigerated enclosure 59 until implantation.

The method for PCL ENF coating on titanium with various surface treatments (machined grooves, TiN ridges, FN immobilized) as provided by the present invention provides at least the following unique features:

1. The machined microgrooves for the protection of the PCL ENF coating on Ti from the applied shear loading during the insertion of the Ti in to the bone.
2. The TiN techniques provided by the present invention can be used for both regular and irregular shape implants.
3. Plasma nitridation improves hardness and ductility that may result in an increased transfer of stress to reduce the effect of stress shielding of bone.
4. The use of oxygen and hydrogen plasma for nanoscale surface modification of Ti, is uniquely used to activate the surface of Ti for the attachment of collagen and fibronectin which bonds the PCL ENF on the Ti surface.
5. The effects of the use of MgO nanoparticles with PCL ENG on the implant-bone interaction may be enhanced to provide better mechanical stability and osseointegration.
6. The groove topography for implant that will provide the optimum biomechanical compatibilities of the implant can be controlled.
7. At the groove, other biological glue such as PMMA cement, fibronectin, collagen is used to attach the PCL ENF.

EXPERIMENTAL ASPECTS

Microgroove and Poly($\epsilon$-Caprolactone)-Collagen Nanofiber Matrix (PCL-CG NFM) Coating Improve the Mechanical Stability and Osseointegration of Titanium Implant.

Figure 6:
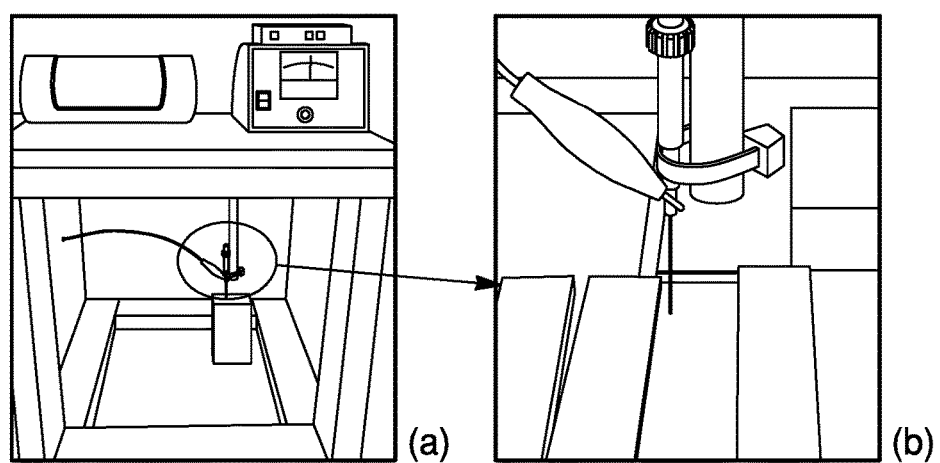
FIG. 6 shows experimental aspects where PCL fiber was produced using ID=0.31 mm gauge needles and ID=0.12 mm gauge needles installed in an electrospin unit by dissolving 5 wt % of PCL beads with acetone, where aligned PCL ENF was collected between two parallel wires.
Figure 7A:
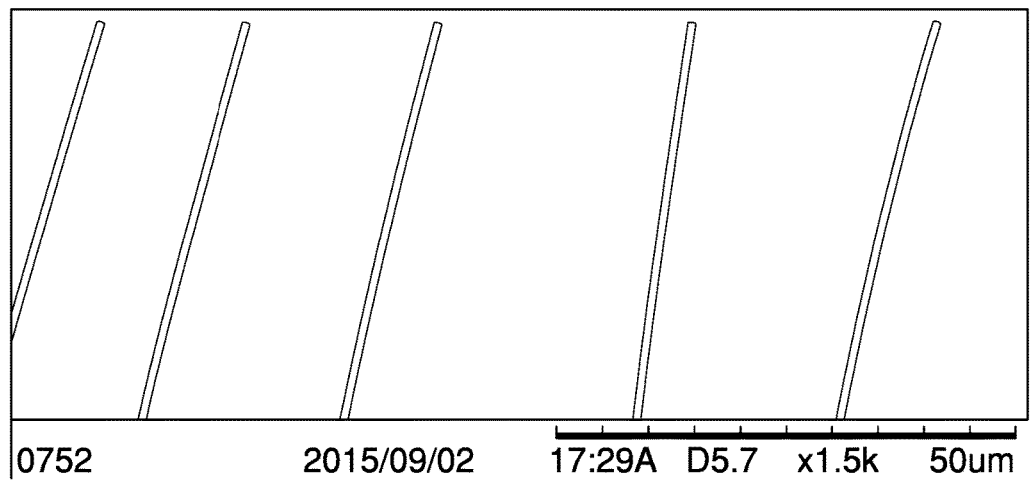
FIG. 7a shows experimental aspects where the average diameters of the fibers found from scanning electron microscope (SEM) images were 518 nm.
Figure 7B:
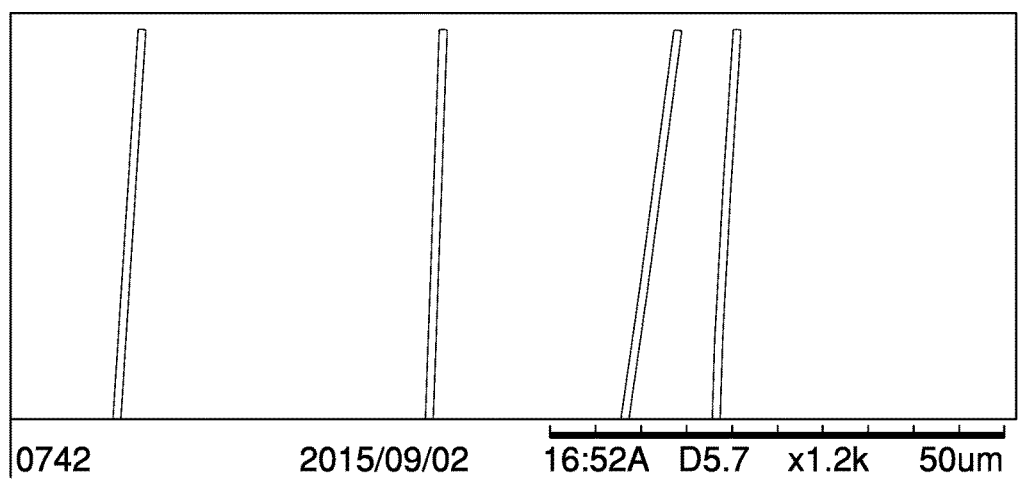
FIG. 7b shows experimental aspects where the average diameters of the fibers found from scanning electron microscope (SEM) images were 305 nm, where the fibers were attached with MgO nanoparticles.

The method of the present invention providing machining of microgroove on Ti and filling the grooves with ECM made with PCL-CG was proven through experimentation by the Applicant to be successful in increasing the in vivo mechanical stability and promoting osseointegration on Ti implants. The automatic production of groove by TiN as disclosed for the present invention increases scalability of the technique for commercialization by optimizing the groove topography using nanofabrication techniques, which will lead to design of better performing clinical implants. Through experimentation, the Applicant developed the methods of the present invention shown in FIG. 6 at (a) and enlarged for viewing at (b). PCL solution may be prepared by ultrasonic (Sonics & Materials, Inc., model # Vibra-cell VCX 130) mixing of 7.69 wt % of PCL pellets (pellet size~3 mm, average Mn 80,000) with acetone (laboratory reagent ≥99.5%). The sonication process may be carried out at approximately 60° C. for 30 minutes. The solution may be poured into a glass syringe in an infusion pump (Harvard Apparatus, mode # PHD ULTRA) for fiber production. PCL fibers may be ejected from the glass syringe via charged needle (23 G blunt needle, aluminum hub, 1" length, model # BX 25). The needle may be charged by high voltage power source (Gamma High Voltage Research, Inc., model # ES 30 series). Two different diameters of PCL fiber were produced using (ID=0.31 mm) and (ID=0.12 mm) gauge needles deployed in the electrospin unit (FIG. 5, 57). Aligned PCL ENF was collected between two parallel wires (FIG. 4, 45). The average diameters of the fibers determined from scanning electron microscope (SEM) images were 518 nm (FIG. 7*a*) and 305 nm (FIG. 7*b*), respectively. Six layers of aligned ENF were coated on Ti by rotating the Ti rod with constant speed. Ti were implanted into rabbit femur and the mechanical stability was measured by a pullout tension test.

Referring now to FIG. 8, the image shows a fabricated samples with grooves 82 made by machining. The image shows a fabricated samples with grooves made by machining and depositing PCL ENF on the grooves 83. Nanofiber matrix is deposited along the groove 83 to enhance the mechanical stability and osseointegration of the implant with the host tissue and solve the implant poor fixation problem. A set of parallel microgrooves 82 is created on Ti at the circumferential direction to increase the surface area of implant in contact with bone and to protect the NFM made with Polycaprolactone (PCL) electrospun nanofiber (ENF) and collagen at the groove 83 from physiological loading.

Figure 9A:
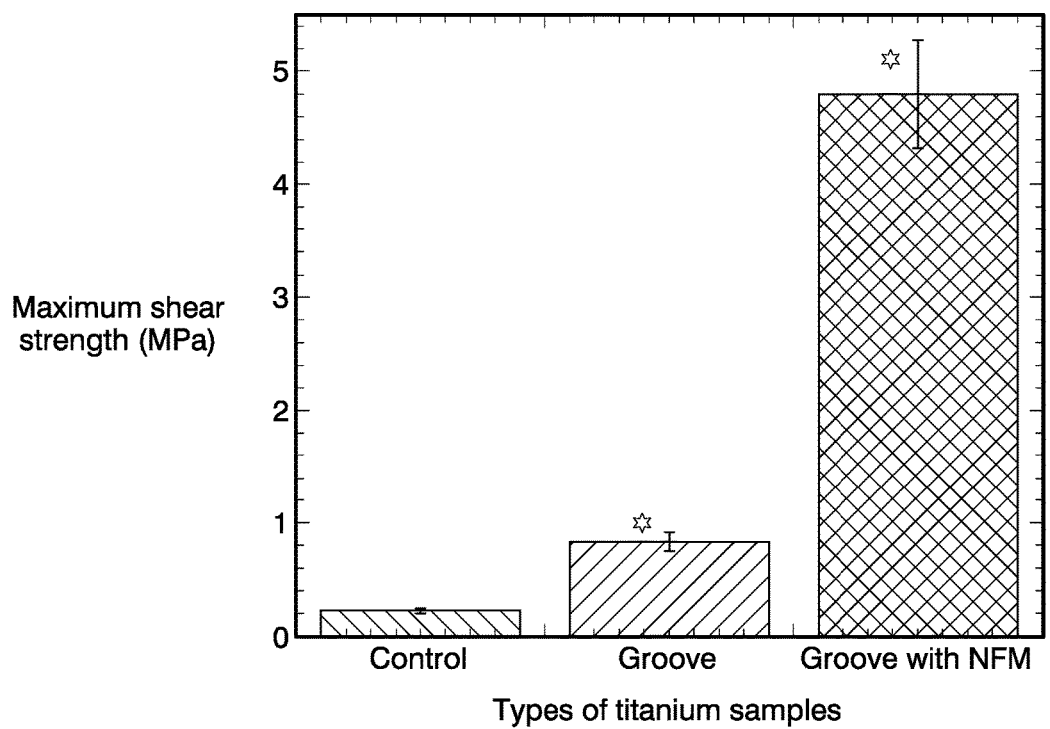
FIG. 9a shows experimental aspects where mechanical test results on in vivo titanium/bone sample show that the amount of force required for breakage of titanium from bone on fiber coated Ti is higher than control and only groove.

Referring now to FIG. 9*a*, the experimental results show that the mean values of shear strength were 3 times higher for grooved Ti samples (0.84±0.3 MPa, n=6) compared to control samples, (0.26±0.09 MPa, n=6), although the difference was not statistically significant ($p>0.05$).

Figure 9B:
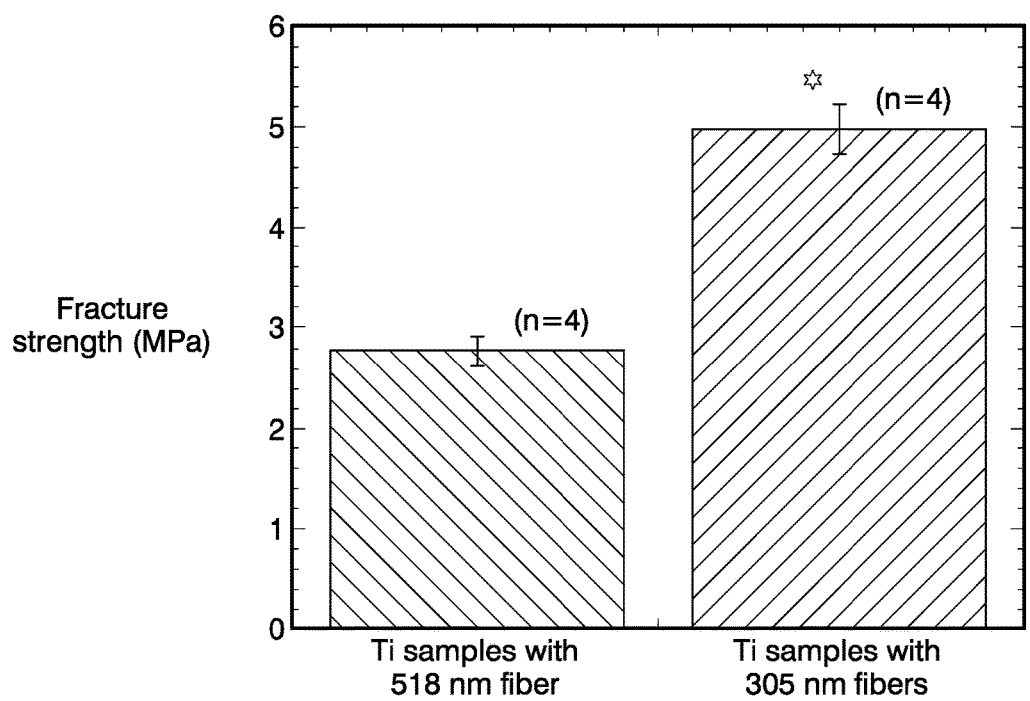
FIG. 9b shows experimental aspects where mechanical test results on in vivo titanium/bone sample show that the amount of force required for breakage of titanium from bone on nanosize fiber coated Ti is higher than micron size fiber coated Ti.

Referring now to FIG. 9*b*, comparing fracture strength results of grooved Ti samples coated with CG-PCL NFM, demonstrates that the ultimate shear strength of NFM coated grooved samples (4.79±0.39 MPa, n=6) were higher (more than 18 times) compared to control samples ($p<0.05$). No statistically significant differences of diameters among the sample group were observed ($p>0.05$). Also there was no statistically significant differences of the length of implant in contact with bone among the sample group ($p>0.05$). Therefore, the surface coating of Ti samples by CG-PCL NFM had a significant effect on the shear strength of the samples. Pullout tension tests result (FIG. 9*b*) showed that the fracture strength of Ti samples having groove with 305 nm diameters of nanofiber are 1.79 times higher than Ti samples having groove with 518 nm diameters of nanofiber.

Figure 10:
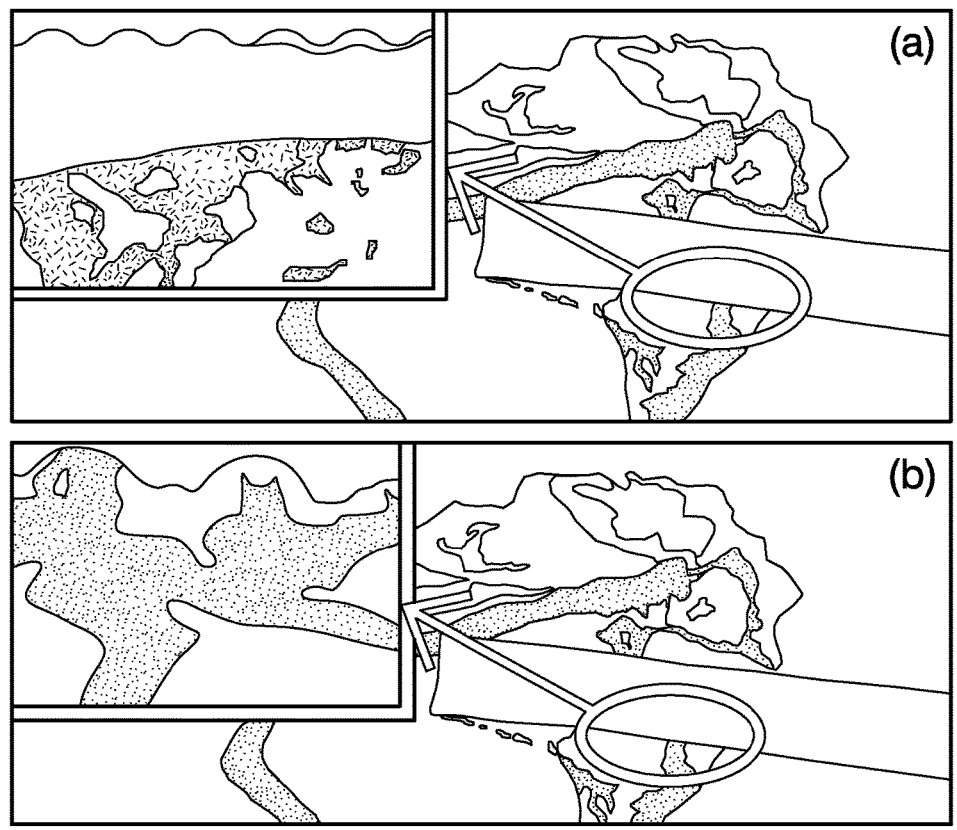
FIG. 10 shows experimental aspects where histomorphometric analysis results (and Table 1) using Sanderson rapid bone stain show that the amount of bone and tissue growth on only groove Ti is less than on (b) grooves with PCL-CG NFM coated Ti.

Referring now to FIG. 10, sectioning, staining, and imaging for histomorphometric analysis was done at pathology core research laboratory in the University of Alabama at Birmingham (UAB). Histomorphometric analysis results (FIG. 10 and Table 1) using Sanderson rapid bone stain show that the amount of bone and tissue growth on ECM coated Ti is higher than control and fiber diameter in ECM has an effect on bone growth. Experimental aspects where staining of uncalcified Ti-bone samples include only grooves as shown in image (a). Experimental aspects where staining of uncalcified Ti-bone samples include groove with 308 nm PCL ENF-CG as shown in image (b). In images, older bone has a lighter gray (pink in color image) and new bone stains dark grey (red in color image), and connective tissue is stained in white. The histological examination shows the total new bone area of a Ti implant significantly increased with the application of PCL-CG NFM.

TABLE 1

Histomorphometric analysis data for a randomly selected Ti sample with only groove; Ti samples having groove with 518 nm and 305 nm diameters of ENF.

| Histological analysis parameters | Only groove | Groove with 518 nm ENF | Groove with 305 nm ENF |
|---|---|---|---|
| Average Groove Depth (μm) | 75.44 | 50.27 | 71.44 |
| Total Bone to Implant sf. (mm) | 7.20 | 20.61 | 12.69 |
| % Bone to Implant Contact (%) | 39.78 | 90.60 | 62.18 |
| Total New Bone Ar. (mm$^2$) | 0.019 | 0.294 | 0.359 |
| Tt Cortical Bone Ar. (mm$^2$) | 0.000 | 0.262 | 0.149 |
| Cortical Bone Surface (mm) | 0.00 | 7.81 | 3.59 |
| New Bone Surface (mm) | 1.29 | 13.12 | 11.23 |
| Total Tissue Area—ROI (mm$^2$) | 1.84 | 2.17 | 1.939 |
| Tt. BV/TV (%) | 1.01 | 25.63 | 26.18 |
| Tt. New Bone/TV (%) | 1.01 | 13.54 | 18.52 |
| Tt. Cortical Bone/TV (%) | 0.00 | 12.09 | 7.66 |

Figure 11A:
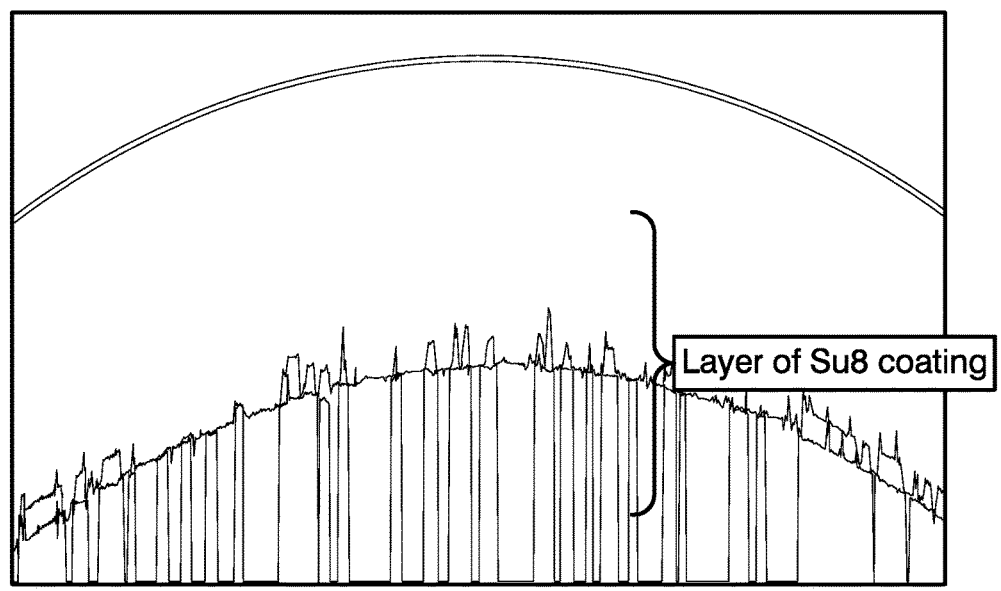
FIG. 11a shows the confocal microscope image of Su8 coated Ti. Su8 coating was applied circumferentially. The figure shows uniform thickness of Su8 coating material.
Figure 11B:
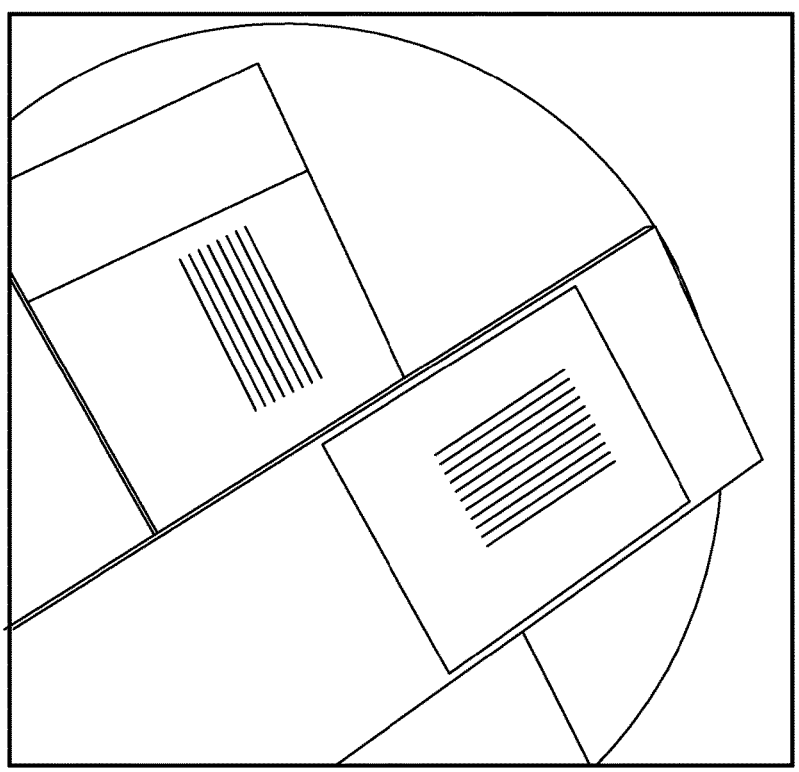
FIG. 11b shows the mask used for creating channels on Su8 coated Ti.
Figure 11C:
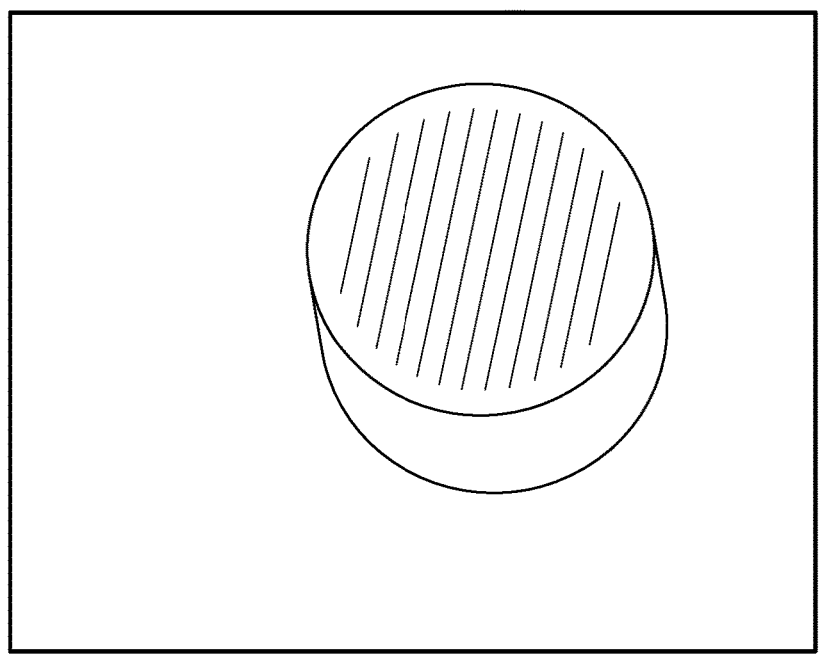
FIG. 11c shows the 3D linear grooves created on the 10 mm diameter Ti surface covered with Su8 coating material.
Figure 11D:
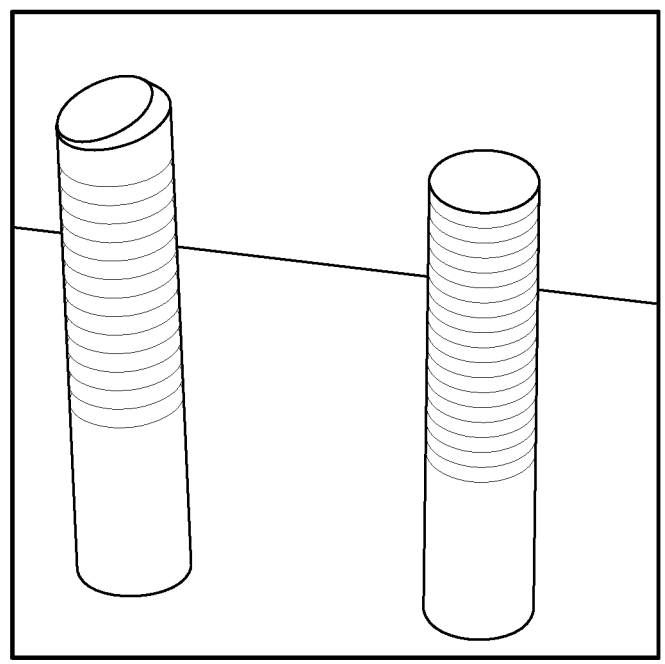
FIG. 11d shows the 3D circumferential grooves created on the 2 mm diameter Ti surface covered with Su8 coating material.

Fabrication of TiN Ridge on Ti:

The process of the present invention was demonstrated to provide a method for fabrication of 50 linear TiN ridges for the 10 mm diameter test samples and 30 circumferential TiN ridges for the 2 mm diameter test samples using photolithography and plasma nitrogen deposition technique (FIG. 3). A 16 μm thin film of Su8 photoresist covers the Ti surface uniformly by spin coating the photoresist on Ti (FIG. 11a). A mask with channels (FIG. 11b) is placed on Ti and exposed for UV etching to create 3D textures at the sites. FIG. 11c and FIG. 11d shows the fabricated 3D Su8 textures on Ti. Research-grade nitrogen gas can be spattered on the Ti surface to create TiN coating. The TiN ridges is visible upon removal of Su8 by a photoresist removing chemical (RemoverPG).

Figure 12:
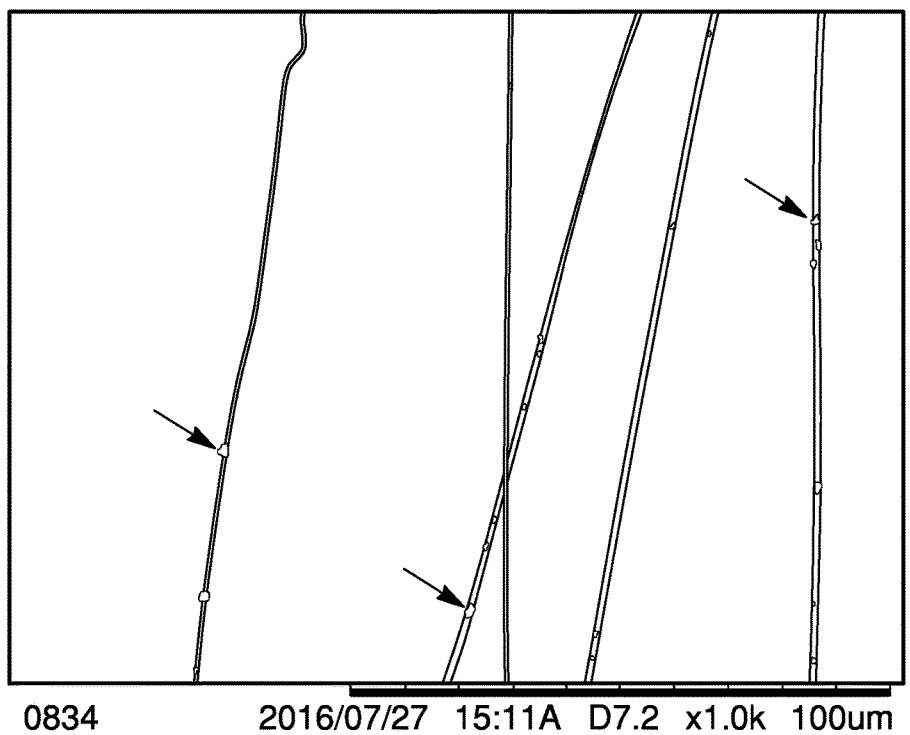
FIG. 12 shows the scanning electron microscope (SEM) image of MgO NP tethered with PCL nanofiber.

Immobilization of MgO NP on PCL ENF:

The process of the present invention was demonstrated to provide a method for fabrication of MgO NP tethered PCL ENF. MgO NPs was dissolved in acetone. A 5 wt. % of MgO NPs was accurately weighed and sonicated for 30 minutes to properly disperse in acetone. PCL beads will be added to the above solution so that the final solution contains 7.9 wt. % PCL and the mixture was sonicated again for 30 minutes. MgO-PCL solution was taken in glass syringes and electrospun. The fibers were collected between two parallel plate collectors. To collect multiple layers of fiber, an acrylic hollow cylindrical substrate was used to touch the aligned fiber stream, then lower it and rotate the substrate 90° and repeat the process to collect another layer. The fiber was viewed under SEM where the tethering of MgO with PCL fiber was clearly visible (marked by black arrows in FIG. 12).

Rat osteoblast cells was cultured in standard culture conditions (37° C. in a 5% CO2 incubator on tissue culture dishes) using DMEM/high glucose+5% FBS and 1% ABAM (Sigma Chemical). Cells were dissociated using 1× trypsin/EDTA solution (Sigma Chemical) for 5 minutes at room temperature, followed by serum inactivation. Cell adhesion, proliferation, differentiation and protein adsorption tests were conducted on PCL-CG NFM and MgO-PCL-CG NFM coated Ti samples. In short, osteoblast cells were seeded at a density of 70,000 cells/ml on each group of Ti samples in a custom-made silicone well-plate. Cells were then cultured for 48 hours to allow cell adhesion and proliferation on the Ti surface. Parallel samples similar to those tested for adhesion and proliferation were cultured for 3 weeks and prepared for immunostaining to determine hydroxyapatite mineralization and osteonectin adsorption. A Click-iT® EdU stain was used to evaluate cell adhesion and proliferation assay for each sample according to vendor's protocol. This 48-hour assay involves the addition of EdU, or 5-ethynyl-2'-deoxyuridine, to each well after the initial 24 hour incubation. The EdU is a modified thymine nucleotide that contains a terminal alkyne51. After a total of 48 hours, the cells were fixed with paraformaldehyde and stained with Alexa-488. The terminal alkyne in the EdU reacts with the azide in Alexa-488, which cause the proliferated cells that incorporate the EdU tag to fluoresce green under fluorescent microscopy. An OsteoImage™ mineralization assay kit from Lonza was used according to vendor's protocol. For the protein adsorption test, osteonectin was used as the primary antibody (clone AON-1; Developmental Studies Hybridoma Bank) and goat anti-mouse rhodamine (red) was used as the secondary antibody. For proliferation, mineralization, and protein adsorption tests, nuclei were counterstained with DAPI stain (blue). The qualitative and quantitative measurements of cell viability on the treated Ti surfaces was conducted from images captured with an Olympus DP72 camera and CelSens software. Cell adhesion on the surface of all types of Ti samples was analyzed for the qualitative measurement of cell viability. The number of cells adhered and the number of cells proliferated after adhesion to each sample was determined from the captured images using the ImageJ software program (http://imagej.nih.gov/ij/). Cell densities on NFM-coated Ti samples was compared to the control Ti samples for the quantitative measurement of cell adhesion and percentage of proliferation. The ratio of mineralized and osteonectin stain area over total area of the image field was used to compare mineralization and osteonectin activities between control and NFM coated Ti samples, respectively. To identify focal adhesion structures, samples were cultured in the same conditions as for the proliferation and differentiation stains; however, upon harvest the samples were fixed using 3% paraformaldehyde and 0.2% Triton-X-100 prior to staining. Samples were stained for 1 hour with mouse anti-human vinculin (clone h-VIN1; EMD Millipore Sigma), followed by a secondary goat anti-mouse Alexa 488 (Thermo Fisher Molecular Probes). Stained samples were inverted onto large coverslips for visualization using 100× oil immersion on an Olympus IX-71 microscope. Images were captured using an Olympus DP72 camera equipped with CelSens software. Subsequent quantification was done using ImageJ software using a published protocol48 with modifications (manuscript in preparation).

Figure 13A:
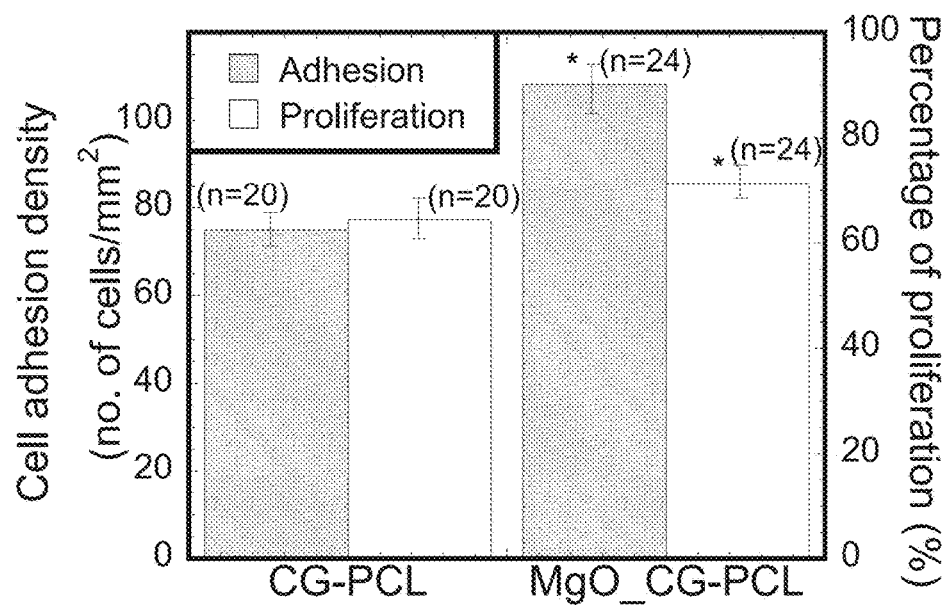
FIG. 13a shows the cell adhesion/proliferation results of the in vitro cytocompatibility test of MgO NP incorporated PCL-CG NFM. In the image * means $p<0.05$ compared to CG-PCL.
Figure 13B:
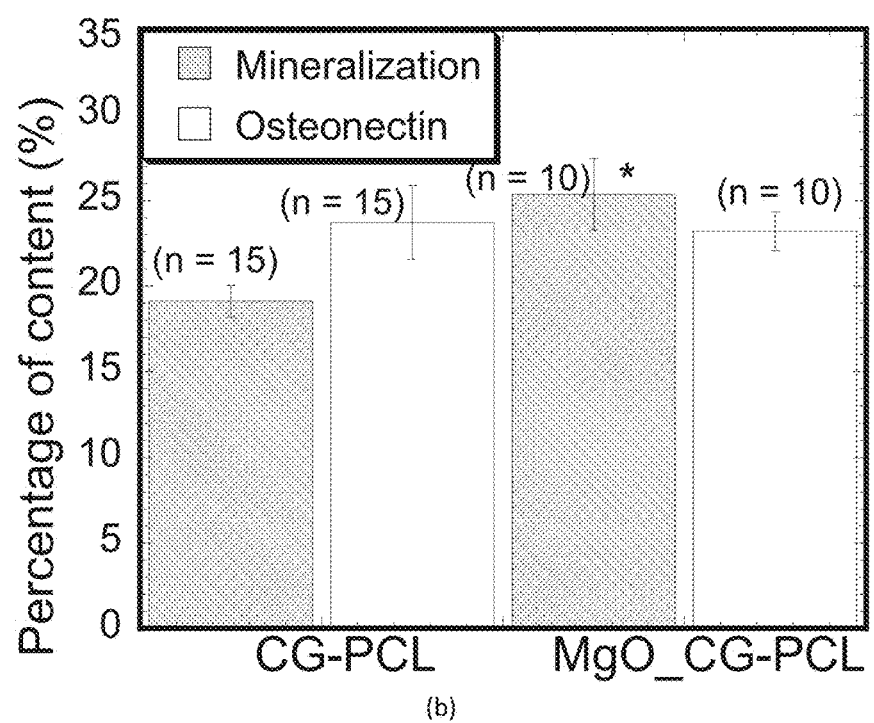
FIG. 13b shows the mineralization/protein adsorption assay results of the in vitro cytocompatibility test of MgO NP incorporated PCL-CG NFM. In the image * means $p<0.05$ compared to CG-PCL.

The experimental results indicate that cell adhesion/proliferation (FIG. 13a), and mineralization/protein adsorption (FIG. 13b) of MgO NP added CG-PCL NFM coated Ti was significantly higher compared to CG-PCL NFM (p<0.05). Mechanical results showed that shear strength of Ti with bone for MgO added CG-PCL NFM coated (5.97±0.65 MPa, n=6) was higher compare to fracture strength of Ti CG-PCL NFM (4.79±0.39 MPa, n=6) (p>0.05).

Figure 14:
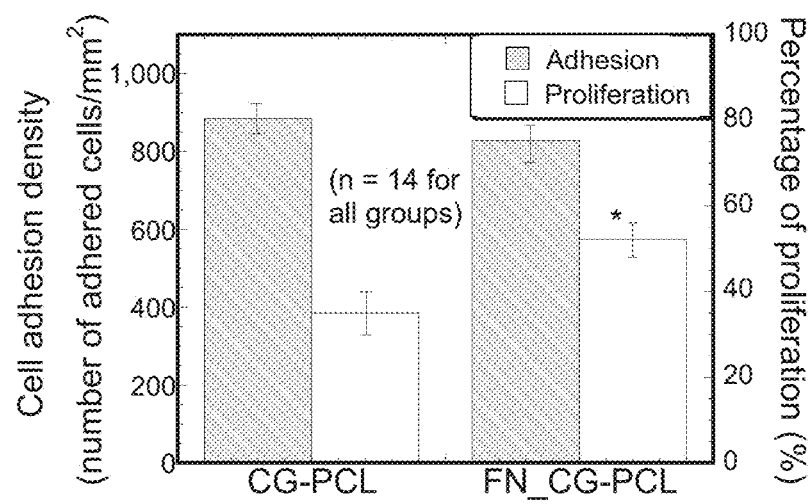
FIG. 14 shows the in vitro osteoblast cell adhesion and proliferation test results of PCL-CG NFM coated Ti without and with FN.

Immobilization of Fibronectin on Ti:

The process of the present invention was demonstrated to provide a method for immobilization of FN on Ti surface using the process as shown in FIG. 5. FN is a multifunctional protein most abundantly found in the extracellular matrix (ECM) under dynamic remodeling conditions such as bone healing and development. FN serves as a biological glue mediating interaction between cells and ECM proteins. FN contains a CG binding domain, so it can be polymerized into CG-PCL NFM. FN has a large binding domain for attaching growth factors such as bone morphogenetic protein (BMP) and transforming growth factor (TGF). Cell viability tests were conducted on CG-PCL NFM coated samples with and without the plasma FN coating on Ti according to the same method as discussed above. Results showed reduced amount of cell attachment ($p>0.05$), but significant improvement of cell proliferation in NFM due to FN coating on Ti ($p<0.05$) (FIG. 14) suggesting that FN coating on Ti can further improve the biological functions of our NFM.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. A process providing a method for coating a titanium (Ti) biomedical implant with nanofiber including the steps:
    polishing a surface of said implant;
    amending said surface effecting at least one of groves and ridges;
    exposing said surface to plasma $O_2$;
    applying a collagen solution to said surface;
    producing electrospun nanofiber (ENF) made with at least Polycaprolactone (PCL);
    depositing said ENF on said surface within said at least one of groves and ridges;
wherein said ENF and collagen form a nanofiber matrix (NFM), and said NMF is adapted to bond within said at least one of grooves and ridges.

2. The method of claim 1, wherein said at least one of grooves and ridges are made using any of machine sawing, laser indentation, and titanium nitride (TiN) ion deposition by a plasma nitride deposition technique.

3. The method of claim 1, wherein said ENF are collected on parallel collectors and substantially aligned between said collectors.

4. The method of claim 1, further comprising coupling magnesium oxide nanoparticles (MgO NPs) and fibronectin (FN) immobilized NFM coating on said surface.

5. A process providing a method for coating a titanium (Ti) biomedical implant with nanofiber including the steps:
    providing said implant;
    polishing a surface of said implant;
    amending said surface effecting at least one of groves and ridges;
    exposing said surface to plasma $O_2$ in a low pressure reactive ion etching system;
    applying a collagen solution to said surface;
    producing electrospun nanofiber (ENF) made with at least Polycaprolactone (PCL);
    depositing said ENF on said surface positioned within said at least one of grooves and ridges;
wherein said ENF and collagen (CG) form a nanofiber matrix (NFM), and
wherein said at least one of grooves and ridges are adapted to at least mitigate physiological loading of said NFM.

6. The method of claim 5, further comprising coupling magnesium oxide nanoparticles (MgO NPs) and fibronectin (FN) immobilized NFM coating on said surface.

7. The method of claim 5, further comprising adapting said NFM to act as resource for other bone growth molecules (rhBMP, TGF-$\beta$) and antimicrobial agents (ZnO, Ag) to the adjoining bone tissue to improve osseointegration with said surface.

8. A titanium (Ti) biomedical implant produced by a method comprising:
    polishing a surface of said implant;
    amending said surface effecting at least one of groves and ridges at the circumferential direction to increase the surface area of said implant in contact with bone;
    exposing said surface to plasma $O_2$ in a low pressure reactive ion etching system;
    applying a collagen solution to said surface;
    depositing electrospun nanofiber (ENF) made with at least Polycaprolactone (PCL) on to said surface and positioned within said at least one of grooves and ridges;
wherein said ENF and collagen form a nanofiber matrix (NFM), and
wherein said at least one of grooves and ridges are adapted to at least mitigate physiological loading of said NFM.

9. The titanium (Ti) biomedical implant of claim 8, wherein said at least one of grooves and ridges are made using any of machine sawing, laser indentation, and titanium nitride (TiN) ion deposition by a plasma nitride deposition technique.

10. The titanium (Ti) biomedical implant of claim 8, wherein said ENF are collected on parallel collectors and substantially aligned between said collectors.

11. The titanium (Ti) biomedical implant of claim 8, further comprising coupling magnesium oxide nanoparticles (MgO NPs) and fibronectin (FN) immobilized NFM coating on said surface.

12. The titanium (Ti) biomedical implant of claim 8, wherein said NFM is made by applying said collagen layer with multiple layers of said ENF.

13. The titanium (Ti) biomedical implant of claim 8, adapted with one of linear TiN ridges or circumferential TiN ridges using photolithography and plasma nitrogen deposition techniques.

14. The titanium (Ti) biomedical implant of claim 8, adapted with metal oxide nanoparticles (MO NPs) tethered by single PCL nanofibers.

15. The titanium (Ti) biomedical implant of claim 8, wherein fibronectin (FN) is coupled with tresyl chloride-activated Ti.

* * * * *